United States Patent
Sayles

(10) Patent No.: US 9,844,260 B2
(45) Date of Patent: Dec. 19, 2017

(54) POWER TOOTHBRUSH WITH MULTIPLE BRISTLE MOTIONS PRODUCING AN AUDIBLE SOUND

(71) Applicant: KONINKLIJKE PHILIPS N.V., Eindhoven (NL)

(72) Inventor: Thomas Jackson Sayles, Fall City, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/104,712

(22) PCT Filed: Dec. 11, 2014

(86) PCT No.: PCT/IB2014/066781
§ 371 (c)(1),
(2) Date: Jun. 15, 2016

(87) PCT Pub. No.: WO2015/092626
PCT Pub. Date: Jun. 25, 2015

(65) Prior Publication Data
US 2017/0000253 A1    Jan. 5, 2017

Related U.S. Application Data

(60) Provisional application No. 61/918,767, filed on Dec. 20, 2013.

(51) Int. Cl.
*A46B 15/00* (2006.01)
*A61C 17/22* (2006.01)
(Continued)

(52) U.S. Cl.
CPC ............ *A46B 15/0028* (2013.01); *A46B 9/04* (2013.01); *A46B 15/0022* (2013.01); *A46B 15/0042* (2013.01); *A61C 17/221* (2013.01); *A61C 17/3445* (2013.01); *A61C 17/3454* (2013.01); *A61C 17/3472* (2013.01); *A61C 17/3418* (2013.01); *A61C 17/3463* (2013.01)

(58) Field of Classification Search
CPC ... A46B 15/0028; A46B 9/04; A46B 15/0022; A46B 15/0042; A61C 17/221; A61C 17/3454; A61C 17/3445; A61C 17/3472
See application file for complete search history.

(56) References Cited

U.S. PATENT DOCUMENTS 3,588,936 A * 6/1971 Duve ................. A61C 17/3472
                                                                15/22.1
5,165,131 A * 11/1992 Staar ...................... A46B 15/00
                                                                15/22.1
(Continued)

FOREIGN PATENT DOCUMENTS

CN        2683063 Y        3/2005
JP       2001346816 A     12/2001
(Continued)

*Primary Examiner* — Shay Karls

(57) ABSTRACT

A power toothbrush includes a handle having a driving system therein. The driving system is responsive to two drive signals. One drive signal produces a clinically effective cleansing action for the teeth, while the other drive signal is arranged to produce audible sounds from the toothbrush which are cognitively stimulating or relaxing.

5 Claims, 1 Drawing Sheet

(51) Int. Cl.
  *A46B 9/04* (2006.01)
  *A61C 17/34* (2006.01)

(56) References Cited

U.S. PATENT DOCUMENTS 5,378,153 A * 1/1995 Giuliani ................. A61C 17/20
                                                          15/167.1
2010/0237720 A1   9/2010 Taylor

FOREIGN PATENT DOCUMENTS

| TW | 201110944 A | 4/2011 |
| TW | 201200701 A | 1/2012 |
| TW | M432326 U | 7/2012 |
| WO | 2007097886 A2 | 8/2007 |
| WO | 2009151461 A1 | 12/2009 |

* cited by examiner

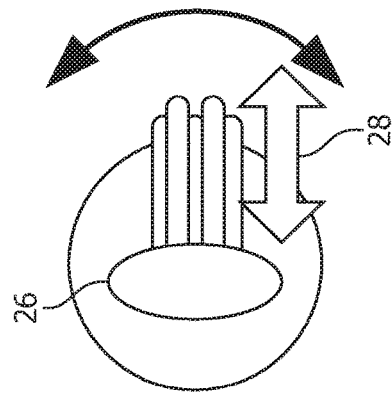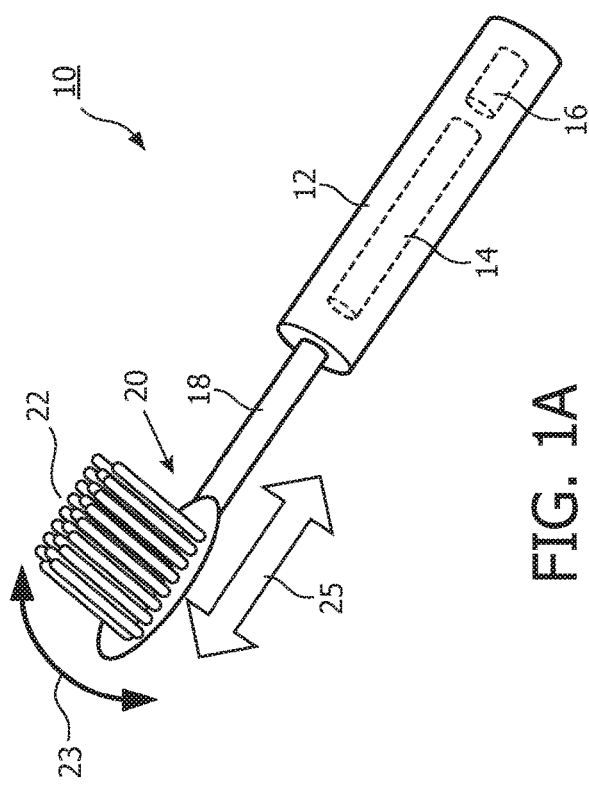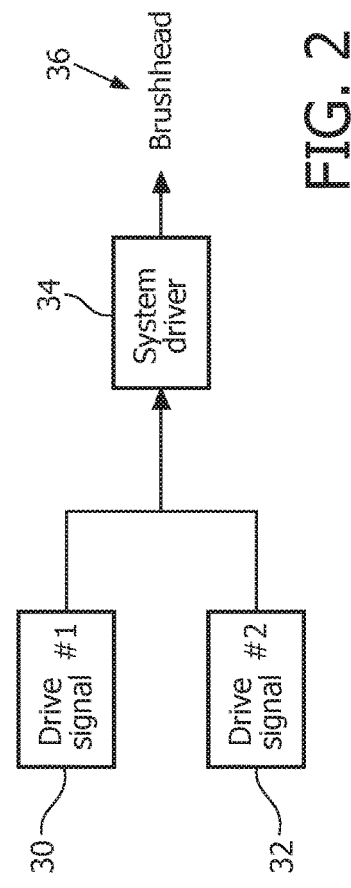
FIG. 1A
FIG. 1B
FIG. 2

POWER TOOTHBRUSH WITH MULTIPLE BRISTLE MOTIONS PRODUCING AN AUDIBLE SOUND

TECHNICAL FIELD

This invention relates generally to power toothbrushes and more specifically to power toothbrushes having multiple bristle motions, with different drive signals for different motions.

BACKGROUND OF THE INVENTION

Many power toothbrushes include multiple brushing modes or routines, typically focusing on general dental care needs, such as soft or gentle brushing, or oral massage, gum care/stimulation, among others. These routines have historically been limited to oral care objectives. In some applications, power toothbrushes are driven to produce complex motions, such as a combination of both sweeping or rotational motion and an axial motion.

It is recognized, however, that oral care is a part of a morning or evening routine, which includes in the evening eventually falling asleep and in the morning waking up. There is hence an interest in not only addressing oral care during those times, but also in addressing cognitive issues, such as reducing restlessness in the evening and increasing alertness in the morning. It would be desirable if both the desired oral care and the cognitive effects could be accomplished in a single appliance.

SUMMARY OF THE INVENTION

Accordingly, a power toothbrush comprises: a handle portion; a brushhead having a set of bristles at the distal end thereof; a first drive signal source producing a first bristle motion having an effective cleansing action for a user's teeth; a second drive signal source producing a second bristle motion with an audible sound which produces a cognitive stimulating or relaxing effect, wherein the first and second drive signals are combined to produce a combined drive signal; and a drive system within the handle portion responsive to the combined drive signal to produce a multiple bristle motion, producing a cleansing effect and audible sounds which produce a cognitive effect.

BRIEF DESCRIPTION OF THE DRAWINGS

FIGS. 1A and 1B show simplified diagrams of power toothbrushes having multi-motions of the brushheads.

FIG. 2 is a simplified block diagram of the brushhead driving system incorporated in the power toothbrush of the present invention.

BEST MODE FOR CARRYING OUT THE INVENTION

FIG. 1A is a simplified view of a power toothbrush, shown generally at 10. The power toothbrush includes a handle or body portion 12 within which is positioned a drive system 14 and a power source 16, which can be, for instance, a battery, which may be rechargeable. The drive system drives or extends through a neck portion 18 of the toothbrush which extends from the handle 12. At the distal end of the neck 18 is a brushhead 20. The brushhead includes a set of bristles 22. The power toothbrush 10 is driven to produce multiple motions of the brushhead and bristles. One example of a multiple motion brushhead is shown in FIG. 1A, in which the brushhead and the bristles move in a sweeping motion 23 (back and forth) as well as an axial motion (25) longitudinally of the toothbrush. In another embodiment, shown in FIG. 1B, a brushhead 26 and bristles move with both a sweeping motion 27 and a tapping motion 28, perpendicular to the longitudinal axis of the toothbrush. Other multiple motions are possible.

In the present invention, a first, primary bristle motion of the brushhead/bristles has characteristics which produce effective cleaning. This, for instance, could be a sweeping motion, which is disclosed in U.S. Pat. No. 5,378,153, the contents of which are hereby incorporated by reference. In that patent, the frequency of motion is within the range of 40 Hz-500 Hz, with an amplitude of 0.5-6 mm and a bristle tip velocity of 1.5-2 meters per second. In one specific embodiment, the frequency is 250-270 Hz, with an amplitude of 2.5 mm. Other arrangements can be utilized, as long as the bristle motion produces an effective cleansing effect.

Another bristle motion, referred to as a secondary motion, separate from the first bristle motion, is produced by another, separate drive signal comprising various tones, rhythms, music or other sounds, which can be heard during use of the toothbrush. The variable tones or audible sounds produced by action of the drive system with the two drive signals acting on the brushhead/bristles produce either cognitive stimulation or cognitive relaxation. The secondary bristle motion producing the cognitive effect is independent of the primary bristle motion and does not negatively affect the teeth-cleaning action of the primary bristle motion.

The drive signal/signals producing the cognitive-affecting secondary bristle motion can have various patterns. One pattern is an increasing frequency to produce a cognitive stimulation or wakefulness sound, audible to the user, while another pattern could be a gradually decreasing frequency to produce a cognitive relaxation effect. Generally, the audible sounds will be in the frequency range of 12-20,000 Hz, with a preferred range of 110-3500 Hz. The sounds can change regularly, at specific times in a two-minute brushing event, e.g. every 30 seconds. The sounds could be complex over the brushing period, producing either stimulating sounds/music for cognitive stimulation or wakefulness, or more soothing music or sounds to produce a cognitive relaxation or restfulness. Besides music, the sounds could be other restful sounds, such as the sounds of water and surf, or stimulating sounds, such as various bird sounds or even stormy weather sounds.

The secondary bristle motions produced by action of the drive system will act like an audio speaker, in response to the associated drive signals. The primary bristle motion produces the desired effective cleaning. Both motions are driven at amplitudes such that the combined motions produce a bristle tip velocity greater than 1.5 meters per second and a bristle tip amplitude of 0.5-6 mm, preferably 2-3 mm, for the effective cleaning.

In many cases, the sound produced by action of the appliance with the two drive signals producing primary and secondary bristle motions will feel like an increase in intensity of bristle action from the start of the brushing period to the end thereof, producing a stimulating effect, while the sounds will feel like a decrease in intensity from start of the brushing period to finish thereof, producing a cognitive/mental relaxation effect.

FIG. 2 shows a simplified view of the drive signal system described above. The drive signal No. 1, referred to as a primary drive signal, is shown at 30, and produces the teeth cleaning effect at the desired effective frequency. Drive signal No. 2, referred to as a secondary drive signal and referenced at 32, is the source of the variable sound, music, etc. which results in the cognitive stimulation/relaxation effect. These two drive signals are combined to form a combined drive signal for the system driver referred to at 34, which drives the brushhead 36 with the multiple bristle motion, shown for example in FIGS. 1A and 1B, or other combinations of motions. The two motions, in two or more directions, are driven at such amplitudes that the combined motion produces a bristle tip velocity greater than 1.5 meters per second and an amplitude of between 0.5 mm and 6 mm. The audible sound, produced from the appliance by this arrangement results in a cognitive effect, either relaxing or stimulating.

Accordingly, a new toothbrush has been disclosed which has multiple bristle motions, in which one bristle motion produces effective teeth cleaning, while the combined action of another bristle motion produces audible sounds which result in a cognitive stimulating or relaxing effect.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A power toothbrush, comprising:
   a handle portion;
   a brushhead having a set of bristles at the distal end thereof;
   a first drive signal source configured to output a second drive signal used for producing a first bristle motion having an effective cleansing action for a user's teeth;
   a second drive signal source configured to output a second drive signal used for producing a second bristle motion with an audible sound for a cognitive stimulating or relaxing effect, wherein the first and second drive signals are combined into a combined drive signal; and
   a drive system within the handle portion and coupled to the brushhead, wherein responsive to the combined drive signal, the drive system is configured to produce multiple primary and secondary bristle motions, which result in a cleansing effect and audible sounds for the cognitive stimulating or relaxing effect, wherein for the cognitive stimulating effect, audible sounds produced by the drive system on the brushhead increase in intensity from a start of a brushing event to an end thereof, and wherein for the cognitive relaxing effect, an intensity of the audible sounds decreases between a start and end of the brushing event.

2. The power toothbrush of claim 1, wherein an effective bristle motion of the multiple primary and secondary bristle motions comprises a frequency range of 40 Hz-500 Hz, an amplitude range of 0.5-6 mm and a bristle tip velocity greater than 1.5 m/s.

3. The power toothbrush of claim 1, wherein a first bristle motion of the multiple primary and secondary bristle motions comprises a first clinically effective bristle motion that includes a sweeping motion, and a second bristle motion of the multiple primary and secondary bristle motions comprises either an axial motion or a tapping motion of the set of bristles.

4. The power toothbrush of claim 1, wherein the audible sounds include music.

5. The power toothbrush of claim 1, wherein the audible sounds include a rhythm variation within each successive portion of a brushing event.

\* \* \* \* \*